United States Patent [19]
Minogue

[11] Patent Number: 5,620,483
[45] Date of Patent: Apr. 15, 1997

[54] PORTABLE PHYSIO-THERAPY APPARATUS

[75] Inventor: Conor M. Minogue, Kinvarra, Ireland

[73] Assignee: BMR Research & Development Limited, Bunberg, Ireland

[21] Appl. No.: 423,521

[22] Filed: Apr. 17, 1995

[51] Int. Cl.$^6$ ........................................... A61N 1/08
[52] U.S. Cl. ........................ 607/115; 607/145; 128/741
[58] Field of Search ........................... 607/115, 46, 145, 607/149, 30; 128/734, 741

[56] References Cited

U.S. PATENT DOCUMENTS

| | | | |
|---|---|---|---|
| 4,365,633 | 12/1982 | Loughman et al. | 607/30 |
| 5,397,338 | 3/1995 | Grey et al. | 607/115 |
| 5,487,759 | 1/1996 | Bastyr et al. | 607/115 X |

Primary Examiner—Angela D. Sykes
Assistant Examiner—Ryan Carter

Attorney, Agent, or Firm—Woodcock Washburn Kurtz Mackiewicz & Norris

[57] ABSTRACT

A physio-therapy apparatus for applying electrical stimulation to a human patient comprising a two-part portable housing. The first housing portion contains a memory for storing a plurality of therapy programs each defining the parameters of electrical signals to be applied to the patient according to that program, first electrical connector means for connecting external stimulation electrodes to the housing, and a microprocessor for driving the electrodes according to a selected one of the stored programs. The second housing portion has a plurality of manual control elements in the form of keys for controlling the microprocessor to select a particular stored program and/or to modify electrical signal parameters of at least one stored program. The second housing portion is detachably connected to said first housing portion by a second electrical connector means whereby a selected program cannot be changed and/or said electrical signal parameters cannot be modified without said second housing portion being attached to said first housing portion.

6 Claims, 2 Drawing Sheets

PORTABLE PHYSIO-THERAPY APPARATUS

FILED OF THE INVENTION

This invention relates to a portable physio-therapy apparatus for applying electrical stimulation to a human patient, for example a muscle stimulator.

SUMMARY OF THE INVENTION

The invention provides a physio-therapy apparatus for applying electrical stimulation to a human patient, the apparatus comprising a portable housing having first and second portions, said first housing portion containing a memory for storing at least one therapy program defining the characteristics of electrical signals to be applied to the patient, first electrical connector means for connecting external stimulation electrodes to the housing, and a microprocessor for driving the electrodes according to said at least one therapy program, and said second housing portion having a plurality of manual control elements for controlling the microprocessor to modify at least some of the electrical signal characteristics of said at least one therapy program, wherein said second housing portion is detachably connected to said first housing portion by a second electrical connector means whereby said electrical signal characteristics cannot be modified without said second housing portion being attached to said first housing portion.

BRIEF DESCRIPTION OF THE DRAWINGS

An embodiment of the invention will now be described, by way of example, with reference to the accompanying drawings, in which.

DETAILED DESCRIPTION OF THE PREFERRED EMBODIMENT

Figure 1:
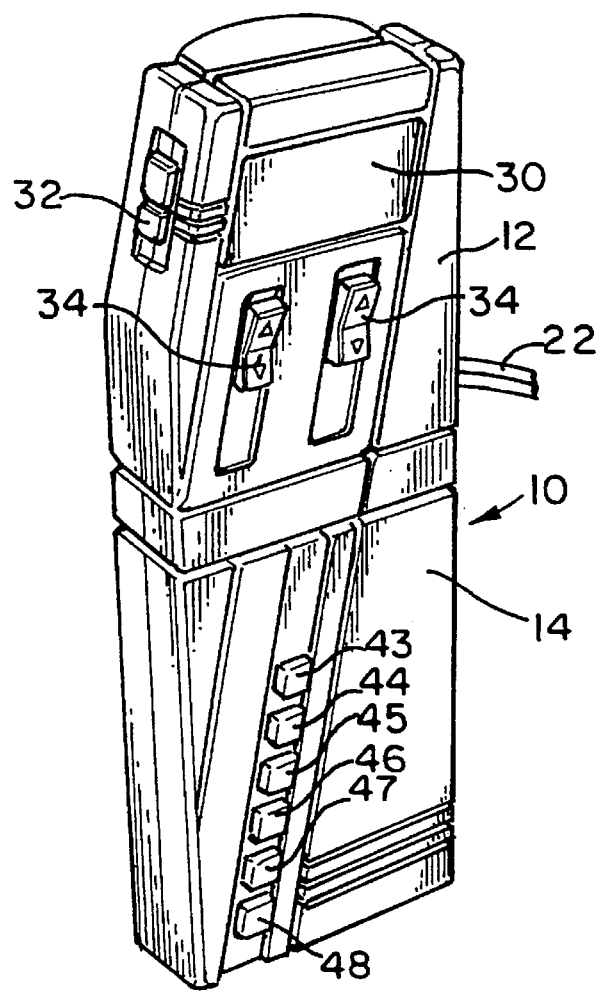
FIG. 1 is a perspective view of an apparatus according to the invention with the first and second housing parts attached.
Figure 2:
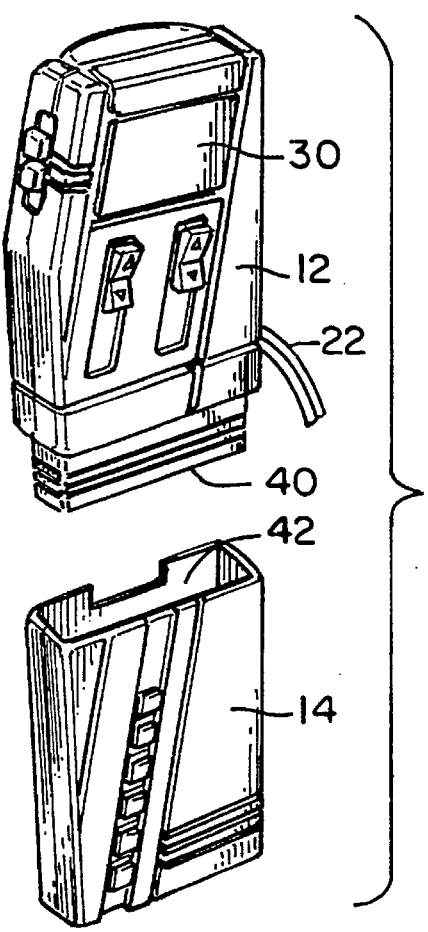
FIG. 2 is a perspective view of an apparatus according to the invention with the first and second housing parts detached.

The embodiment of the invention is a portable muscle stimulation apparatus contained in a housing 10 having first and second portions 12 and 14 respectively. As seen in FIG. 2, the second housing portion 14, which is referred to herein as the Clinical Control Unit, is detachable from the first housing portion 12, which is referred to herein as the Patient Unit. The Patient and Clinical Control Units are each slightly larger than a standard audio cassette.

Figure 4:
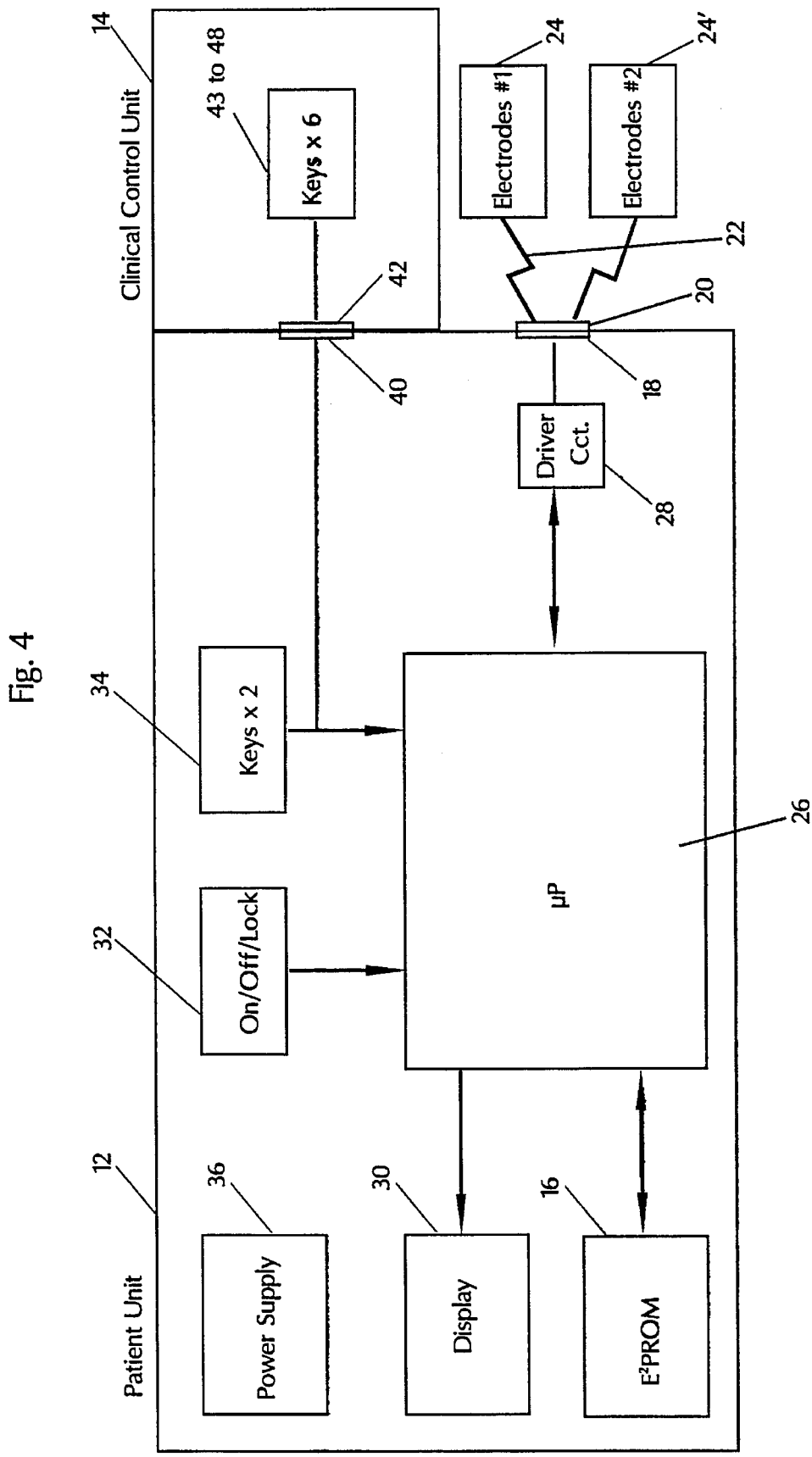

The Patient Unit 12 contains a solid state memory 16 (FIG. 4) in the form of an EEPROM for storing a plurality of therapy programs each defining the parameters of electrical signals to be applied to a patient according to that program. Each stored program defines, for example, the frequency, pulse width, contraction time, relaxation time, ramp up, ramp down and amplitude limit of the electrical signals to be applied to a patient when that program is selected.

Figure 3:
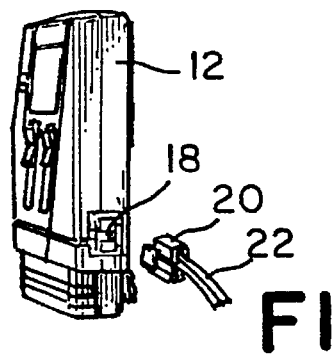
FIG. 3 is a perspective view of the first housing portion from another angle, and FIG.. 4 is a block circuit diagram of the apparatus.

The Patient Unit 12 also includes a jack socket 18 (FIG. 3) to receive a jack plug 20 connected via leads 22 to two pairs of external stimulation electrodes 24 and 24', and a microprocessor 26 for driving the electrodes 24/24', via drive circuitry 28, according to the electrical signal parameters defined by a selected one of the programs stored in the memory 16. The Patient Unit 12 also includes a display screen 30 for displaying various information regarding the stored programs, an on/off/lock switch 32, and two up/down amplitude keys 34, as will be described. The Patient Unit is powered by a rechargeable battery 36.

The Clinical Control Unit 14 detachably connects to the Patient Unit 12 by a multi-pin plug and socket of which the socket part 40 is on the Patient Unit 12 and the multi-pin plug 42 is on the Clinical Control Unit 14. The Clinical Control Unit 14 has a plurality of manual control elements in the form of keys 43 to 48 which, when the Unit 14 is properly attached to the Unit 12 by the plug and socket 40/42, can be used to control the microprocessor 26 to select a particular program and/or modify the electrical signal parameters of certain of the programs. However, when the Clinical Control Unit 14 is detached from the Patient Unit 12 a selected program cannot be changed and/or the parameters of a stored program cannot modified, except to the limited extent provided on the Patient Unit itself as will be described.

Thus the Patient Unit 12 can be "programmed" by a clinician who retains the Clinical Control Unit 14, leaving the patient only with the Patient Unit 12 so that the patient cannot accidentally or deliberately change or override the clinician's settings. Of course, the clinician may have only one Clinical Control Unit 14 for several Patient Units 12.

The operation of the controls will now be described.
1. Patient Unit
Off/On/Lock Switch 32

This is a three-position switch is located on the upper left-hand side of the unit. In the "Off" position, the unit is switched off. In the "On" position, the unit is turned on and the signal amplitude can be adjusted by using the up/down keys 34. In the "Lock" position, the signal amplitude set by the keys 34 is locked at the desired level, preventing accidental override during treatment.
Amplitude Keys 34

These are two color-coded up/down rocker switches to allow independent signal amplitude settings at each pair of electrodes 24/24'. When the Off/On/Lock switch 32 is initially set to the "On" position, the amplitude is zero. Depressing either amplitude key up/down increases/decreases the amplitude in approximately 2% steps of the maximum amplitude. Maintaining the switch depressed causes the amplitude to increment one step every 0.25 seconds.
2. Clinical Control Unit The top five keys 43 to 47 of the Clinical Control Unit are marked Prog, Param, Opt, Rx and Total respectively, and the bottom key 48 is an Enter key. The operation of each key will now be described.
Prog (Program) Key 43

Depressing the "Prog" key 43 causes the display 30 to show the word "PROGRAM" and the program number currently selected. Depressing the right-hand amplitude key 34 up or down causes the display to change between the ten available programs i.e. 0 to 9. The programs have factory default settings, but programs 0 to 4 can be modified. Depressing the "Enter" key 48 selects the program.
Param (Parameter) Key 44

Depressing the "Param" key 44 displays the parameter values of the currently selected program on the display 30. The parameters can be rotated through by depressing the "Param" key repeatedly. In programs 0 to 4 the parameter values can be changed by depressing the right-hand amplitude key 34. Depressing the Enter key 48 will save the required setting. The parameters which can be changed are as following: Frequency, Pulse Width, Contraction Time, Relaxation Time, Ramp Up, Ramp Down, and Amplitude Limit.

Opt (Option) Key 45

The "Opt" key 45 is used to enable or disable optional features of the program selected. There are seven (7) such features available. Depressing the "Opt" key causes the word "OPTION" and the currently selected option number to be displayed on the display 30. The words "ON" and "OFF" will also appear on the display, depending on the option status. Depressing the right-hand amplitude key 34 up/down increases/decreases the option number. Depressing the left-hand amplitude key 34 up/down turns on/off the currently displayed option number. The displayed option refers only to the program which is currently selected. If the program is changed the option must again be selected for that new program. Typical options are single or dual frequency, mono or hi-phase mode and trigger mode (see below).

Rx (Treatment Time) Key 46

Depressing the "Rx" key 46 causes the words "TREATMENT TIME" and a 4-digit timer to be displayed on the display 30. The maximum programmable treatment time is 23 hours, 59 minutes. Depressing the left-hand amplitude key 34 up/down increases/decreases the hours. Depressing the right-hand amplitude key 34 up/down increases/decreases the minutes. If a treatment time of 00.00 is selected, the unit will count upwards until it reaches a preset total treatment time. If a treatment time is specified, the time will be displayed and will count down to 00.00. When the timer reaches 00.00 the stimulus will stop, the display will show the treatment time and a warning beep will indicate to the user that their treatment session is finished. The unit must then be turned off, to reset for another treatment session.

Total (Total Treatment Time) Key 47

The clinician may set a limit on the accumulated treatment time received by the patient over several sessions. This is called the total treatment time. When the Patient and Clinical control Units are attached, the words "TOTAL TREATMENT TIME" and a clock symbol are displayed on the display 30. The total accumulated time the patient has used the unit is also displayed. Depressing the "Total" key 47 will change the display to show the total treatment time which can be set by the clinician. The word "PROGRAM" and the program number will also be displayed. The range of the time is from 00.00 to 9999 hours. Depressing the Enter 48 key will store the total treatment time set by the clinician and zero the accumulated treatment time. Depressing the Total key 47 again will return to the accumulated treatment time display.

Enter Key 48

Depressing the "Enter" key 48 will select the currently displayed program. On programs 0 to 4, parameters can be changed by depressing the Enter key when the chosen parameter is displayed. The selected treatment time and total treatment time are also stored by depressing the Enter key. While option 6 (trigger mode) is turned on, the Enter key when depressed will start the stimulus and when released will stop the stimulus.

Dual Program Operation

The apparatus allows the clinician to prescribe two programs to be used off-site by a patient: program 'A' and program 'B'. The patient can select the required program by means of a slide switch in the battery compartment. To set the Patient Unit for dual program operation the following steps are carried out: Program 'B' is always set first. To set program 'B': a) Select program 1 as described above, b) change parameters and Rx treatment time as required ensuring to depress Enter after each change, and c) change options as required. To set Program 'A': Select another program as described above.

It will be seen that the Patient Unit 12 programming can be modified to include data recording features, to enable for example, recording of the amount of time the patient used the device, on which channels and on which settings etc. The Clinical Control Unit 14 could then be used to display, print or download this information as required.

I claim:

1. A physio-therapy apparatus for applying electrical stimulation to a human patient, the apparatus comprising a portable housing having first and second portions, said first housing portion containing a memory for storing at least one therapy program defining the characteristics of electrical signals to be applied to the patient, first electrical connector means for connecting external stimulation electrodes to the housing, and a microprocessor for driving the electrodes according to said at least one therapy program, and said second housing portion having a plurality of manual control elements for controlling the microprocessor to modify at least some of the electrical signal characteristics of said at least one therapy program, wherein said second housing portion is detachably connected to said first housing portion by a second electrical connector means whereby said electrical signal characteristics cannot be modified without said second housing portion being attached to said first housing portion.

2. A physio-therapy apparatus according to claim 1, wherein said memory stores a plurality of therapy programs, each therapy program defining the characteristics of electrical signals to be applied to the patient according to the respective therapy program, and wherein at least one of said manual control elements on said second housing portion controls the microprocessor to select any one of said therapy programs.

3. A physio-therapy apparatus according to claim 2, wherein said manual control elements permit said electrical signal characteristics of at least one but less than all of said therapy programs to be modified.

4. A physio-therapy apparatus according to claim 1, wherein said first housing portion further includes a display screen for displaying information regarding the therapy programs.

5. A physio-therapy apparatus according to claim 1, wherein at least one manual control element is also provided on said first housing portion to permit the amplitude of signals applied to said electrodes to be varied without said second housing portion being attached to said first housing portion.

6. A physio-therapy apparatus for applying electrical stimulation to a human patient, the apparatus comprising a first portable housing portion containing a memory for storing at least one therapy program defining the characteristics of electrical signals to be applied to the patient, first electrical connector means for connecting external stimulation electrodes to the housing, and a microprocessor for driving the electrodes according to said at least one therapy program, said first portable housing portion further including second electrical connector means for detachably connecting a second portable housing portion to said first portable housing portion, said second portable housing portion having a plurality of manual control elements for controlling the microprocessor to modify at least some of the electrical signal characteristics of said at least one therapy program, whereby said electrical signal characteristics cannot be modified without said second portable housing portion being attached to said first portable housing portion.

* * * * *